United States Patent
Mead (10) Patent No.: US 10,620,220 B2
(45) Date of Patent: Apr. 14, 2020

(54) ASSAY FOR DETECTING FREE LIGHT CHAINS BY CAPILLARY ZONE ELECTROPHORESIS

(75) Inventor: Graham Peter Mead, Birmingham (GB)

(73) Assignee: The Binding Site Limited, Birmingham (GB)

( * ) Notice: Subject to any disclaimer, the term of this patent is extended or adjusted under 35 U.S.C. 154(b) by 1284 days.

(21) Appl. No.: 13/805,737

(22) PCT Filed: Jun. 2, 2011

(86) PCT No.: PCT/GB2011/051044
§ 371 (c)(1),
(2), (4) Date: Apr. 19, 2013

(87) PCT Pub. No.: WO2011/161430
PCT Pub. Date: Dec. 29, 2011

(65) Prior Publication Data
US 2013/0210168 A1     Aug. 15, 2013

(30) Foreign Application Priority Data
Jun. 21, 2010 (GB) .................................. 1010405.7

(51) Int. Cl.
| | | |
|---|---|---|
| *G01N 33/68* | (2006.01) | |
| *G01N 27/447* | (2006.01) | |
| *C07K 16/06* | (2006.01) | |
| *C07K 16/42* | (2006.01) | |
| *G01N 33/561* | (2006.01) | |

(52) U.S. Cl.
CPC ....... *G01N 33/6857* (2013.01); *C07K 16/065* (2013.01); *C07K 16/42* (2013.01); *G01N 27/44726* (2013.01); *G01N 33/561* (2013.01)

(58) Field of Classification Search
None
See application file for complete search history.

(56) References Cited

U.S. PATENT DOCUMENTS

| | | | |
|---|---|---|---|
| 5,228,960 A | 7/1993 | Liu et al. | |
| 5,348,633 A | 9/1994 | Karger et al. | |
| 5,536,382 A | 7/1996 | Sunzeri | |
| 6,780,300 B1 | 8/2004 | Alberto | |
| 2005/0164302 A1* | 7/2005 | Robert | C07K 16/00 435/7.1 |
| 2010/0113752 A1* | 5/2010 | Chaffey | G01N 33/561 530/391.1 |

FOREIGN PATENT DOCUMENTS

| | | | | |
|---|---|---|---|---|
| WO | 2010/049672 | | 5/2010 | |
| WO | WO 2010049672 A2 | * | 5/2010 | ............. C07K 16/42 |
| WO | WO-2010049672 A2 | * | 5/2010 | ............. C07K 16/42 |

OTHER PUBLICATIONS

Schultz et al. ("Rapid Immunoassays Using Capillary Electrophoresis with Fluorescence Detection" Analytical Chemistay, vol. 85, No. 21, Nov. 1, 1993).*
Sebia ("Minicap Immunotyping" Apr. 1, 2009).*
Hafner et al. ("Noncompetitive Immunoassay of Small Analytes at the Femtomolar Level by Affinity Probe Capillary Electrophoresis: Direct Analysis of Digoxin Using a Uniform-Labeled scFv Immunoreagent" Anal. Chem. 2000, 72, 5779-5786).*
Schultz and Kennedy, "Rapid Immunoassays Using Capillary Electrophoresis With Fluorescence Detection," Anal. Chem. 1993, vol. 65, pp. 3161-3165.
Hutchison et al., "Serum free light chain measurement aids the diagnosis of myeloma in patients with severe renal failure," BMC Nephrology, 2008, 9:11.
Iyer et al., Two-Color Capillary Electrophoresis with On-Column Excitation and Wave-Guide Based Fluorescent Detection, 2003, 8(4): p. 41-45.
Zhang et al., Enhancement of signal-to-noise level by synchronized dual wavelength modulation for light emitting diode fluorimetry in a liguid-cor-waveguide icrofluidic capillary electronphoresis system, 2005, Talanta, p. 19-24.
Chen et al., Feasibility Studies for Simultaneous Immunochemical Multianalyte Drug Assay by Capillary Electrophoreis with Laser-Induced Fluorescence, 1994, Clin. Chem, p. 1819-1822.
Heegaard et al., Antigen-antiboyd interactions in capillary electrophoresis, 2002, Journ ofChromatography B, 768: p. 93-103.
Tao et al., On-Line Competitive Immunoassay for Insulin Based on Capillary Electrophoresis with Laser-Induced Fluorescence Detection, 1996, Anal. Chem., 68: p. 3899-3906.
Shimura et al., Affinity Probe Capillary Electrophoresis: Analysis of Recombinant Human Growth Hormone with a Fluorescent Labeled Antibody Fragment, 1994, Anal. Chem., 66: p. 9-15.
Jorgenson et al., Capilly Zone Electrophoresis, 1983, Science, 222: p. 266-272.
Chen, Characterization of charge-modified and fluorescein-labeled antibody by capillary electrophoresis using laser-induced fluorescence; Applicationto immunoassay of low level immunoglobulin A, 1994, Journal of Chormatography A, 680: p. 419-423.
Extended Eurpean Search Report for EP Application No. 17199713. 3, dated Feb. 19, 2018.
Chen et al., "Feasibility studies for simultaneous immunochemical multianalyte drug assay by capillary electrophoresis with laser-induced fluorescence," Clin. Chem., Amer. Assoc. for Clin. Chem., Washington, DC, vol. 40, No. 9, Sep. 1, 1994, pp. 1819-1822.

(Continued)

*Primary Examiner* — Changhwa J Cheu
(74) *Attorney, Agent, or Firm* — Barnes & Thornburg LLP (57) ABSTRACT

The invention provides a method detecting free light chains (FLCs) comprising: (i) providing a sample from a subject; (ii) mixing the sample with an anti-FLC specific antibody, or fragments thereof capable of specifically binding the FLC, to form a mixture; (iii) passing the mixture through a capillary tube by capillary zone electrophoresis (CZE); and (iv) detecting the presence of the antibody or fragment thereof after passage through at least a portion of the capillary tube. Capillary tubes for use in CZE and kits comprising capilliary tubes and at least one anti-FLC antibody are also provided.

11 Claims, 9 Drawing Sheets

(56) References Cited

OTHER PUBLICATIONS

Chen et al., "Characterization of charge-modified and fluorescein-labeled antibody by capillary electrophoresis using laser-induced fluorescence application to immunoassay of low level immunoglobulin A," J. of chromatography, Elsevier Science, Publishers B.V., NL, vol. 680, No. 2, Oct. 7, 1994, pp. 419-423.

Guzman et al., "Effect of buffer constituents on the determination of therapeutic proteins by capillary electrophoresis," J. of Chromatography, vol. 608, (1992), pp. 197-204.

Heegaard et al., "Antigen-antibody interactions in capillary electrophoresis," J. of Chromatography B., vol. 768, (2002), pp. 93-102.

Huang et al., "On-line concentration of microheterogeneous proteins by capillary electrophoresis using SDS and PEO as additives," J. of Proteome Research, vol. 5, No. 2, 2006, pp. 429-436.

Iyer et al., "Two-color capillary electrophoresis with on-column excitation and wave-guide based fluorescent detection," J. of Assoc. for Laboratory Automation, vol. 8, No. 4, Aug. 1, 2003, pp. 41-45.

Relf et al., "Fluorescein isothiocyanate-labeled protein G as an affinity ligand in affinity/immunocapillary electrophoresis with fluorescence detection," Anal. Chem., vol. 66, No. 22, 1994, pp. 4027-4033.

Shimura et al., "Affinity probe capillary electrophoresis: analysis of recombinant human growth hormone with a fluorescent labeled antibody fragment," Anal. Chem., vol. 66, No. 1, Jan. 1, 1994, pp. 9-15.

Tao et al., "On-line competitive immunoassay for insulin based on capillary electrophoresis with laser-induced fluorescence detection," Anal. Chem., vol. 68, No. 22, Jan. 1, 1996, pp. 3899-3906.

Zhane et al., "Enhancement of signal-to-noise level by synchronized dual wavelength modulation for light emitting diode fluorimetry in a liquid-core-waveguide microfluidic capillary electrophoresis system," Talanta, Elsevier, Amsterdam, NL, vol. 68, No. 1, Nov. 15, 2005, pp. 19-24.

\* cited by examiner

Fig. 1 CZE electropherogram of normal human serum

ASSAY FOR DETECTING FREE LIGHT CHAINS BY CAPILLARY ZONE ELECTROPHORESIS

CROSS REFERENCE TO RELATED APPLICATIONS

This application is a U.S. national counterpart application of International Application No. PCT/GB2011/051044 filed Jun. 2, 2011, which claims priority to G.B. Patent Application No. 1010405.7, filed Jun. 21, 2010. The entire disclosures of PCT/GB2011/051044 and G.B. Patent Application No. 1010405.7 are hereby incorporated by reference.

The invention relates to methods for detecting free light chains (FLCs) using capillary zone electrophoresis (CZE), and to kits and components for using in the assay.

The Applicants have for many years studied free light chains as a way of assaying for a wide-range of monoclonal gammopathies in patients. The use of such free light chains in diagnosis is reviewed in detail in the book "Serum Free Light Chain Analysis, Fifth Edition (2008) A. R. Bradwell et al, ISBN 0704427028".

Antibodies comprise heavy chains and light chains. They usually have a two-fold symmetry and are composed of two identical heavy chains and two identical light chains, each containing variable and constant region domains. The variable domains of each light-chain/heavy-chain pair combine to form an antigen-binding site, so that both chains contribute to the antigen-binding specificity of the antibody molecule. Light chains are of two types, κ and λ and any given antibody molecule is produced with either light chain but never both. There are approximately twice as many κ as λ molecules produced in humans, but this is different in some mammals. Usually the light chains are attached to heavy chains. However, some unattached "free light chains" are detectable in the serum or urine of individuals. Free light chains may be specifically identified by raising antibodies against the surface of the free light chain that is normally hidden by the binding of the light chain to the heavy chain. In free light chains (FLC) this surface is exposed, allowing them to be detected immunologically. Commercially available kits for the detection of κ or λ free light chains include, for example, "Freelite™", manufactured by The Binding Site Limited, Birmingham, United Kingdom. The Applicants have previously identified that measuring the amount of free κ, free λ, and/or free κ/free λ ratios, aids the detection of monoclonal gammopathies in patients. It has been used, for example, for the diagnosis of intact immunoglobulin multiple myeloma (MM), light chain MM, non-secretory MM, AL amyloidosis, light chain deposition disease, smouldering MM, plasmacytoma and MGUS (monoclonal gammopathies of undetermined significance). Detection of FLC has also been used, for example, as an aid to the diagnosis of other B-cell dyscrasia and indeed as an alternative to urinary Bence Jones protein analysis for the diagnosis of monoclonal gammopathies in general.

Conventionally, an increase in either the λ or κ light chains is looked for. For example, multiple myelomas result from the monoclonal multiplication of a malignant plasma cell, resulting in an increase in a single type of cell producing a single type of immunoglobulin. This results in an increase in the amount of free light chain, either λ or κ, observed within an individual. This increase in concentration may be determined, and usually the ratio of the free κ to free λ is determined and compared with the normal range. This aids in the diagnosis of monoclonal disease. Moreover, the free light chain assays may also be used for the following of treatment of the disease in patients. Prognosis of, for example, patients after treatment for AL amyloidosis may be carried out.

Serum protein electrophoresis (SPE) has for many years been part of the screening protocol for myeloma and other monoclonal gammopathies and is based on the separation of serum proteins into 6 regions: albumin, α1, α2, β1, β2, and γ under the influence of an electric field: specific bands are formed which are fixed and stained, the concentration of bands can be quantified by densitometry. The sensitivity of this method for monoclonal free light chain (FLC) detection is between 500-2000 mg/L, depending on where the protein migrates. Serum immunofixation electrophoresis (IFE) is a more sensitive method for monoclonal FLC detection than SPE (150-500 mg/L), however it is more time consuming, expensive and not quantitative.

CZE is used in many clinical laboratories for serum protein separation and can be used as an alternative to SPE for the detection of monoclonal gammopathies. Introduced in the 1960's, the technique separates molecules based on their charge to mass ratio inside a narrow capillary (25-200 μm internal diameter) filled with an electrolyte. The capillary tube ("column") has a high surface to volume ratio, and radiates heat readily so samples do not over-heat during the separation. On-column detection of the migrating molecules is accomplished by shining a light source through a portion of the tubing called the detection window and monitoring absorbance at specific wavelengths.

The velocity of migration of an analyte in capillary electrophoresis will also depend upon the rate of electro osmotic flow (EOF) of the buffer solution. EOF is the motion of liquid induced by an applied potential across a capillary tube and is caused by an electrical double layer that forms at the stationary/solution interface. In CZE, the narrow channels are typically made up of silica and silanol groups that form the inner surface of the capillary column.

These silanol groups are ionized above pH 3. Thus, the inner surface of the channel is negatively charged. In solutions containing ions, the cations will migrate to the negatively charged wall. This forms an electrical double layer. When an electrical potential is applied to the column, with an anode at one end of the column and a cathode at another, the cations will migrate towards the cathode. Since these cations are solvated and clustered at the walls of the channel, they drag the rest of the solution with them, even the anions, thus giving rise to the EOF flow. In a typical system, the EOF is directed toward the negatively charged cathode so that the buffer flows through the capillary from the source vial to the destination vial. The EOF will increase with pH until all of the available silanols lining the wall of the capillary are fully ionized. Separated by differing electrophoretic mobilities, analytes migrate toward the cathode.

Figure 1:
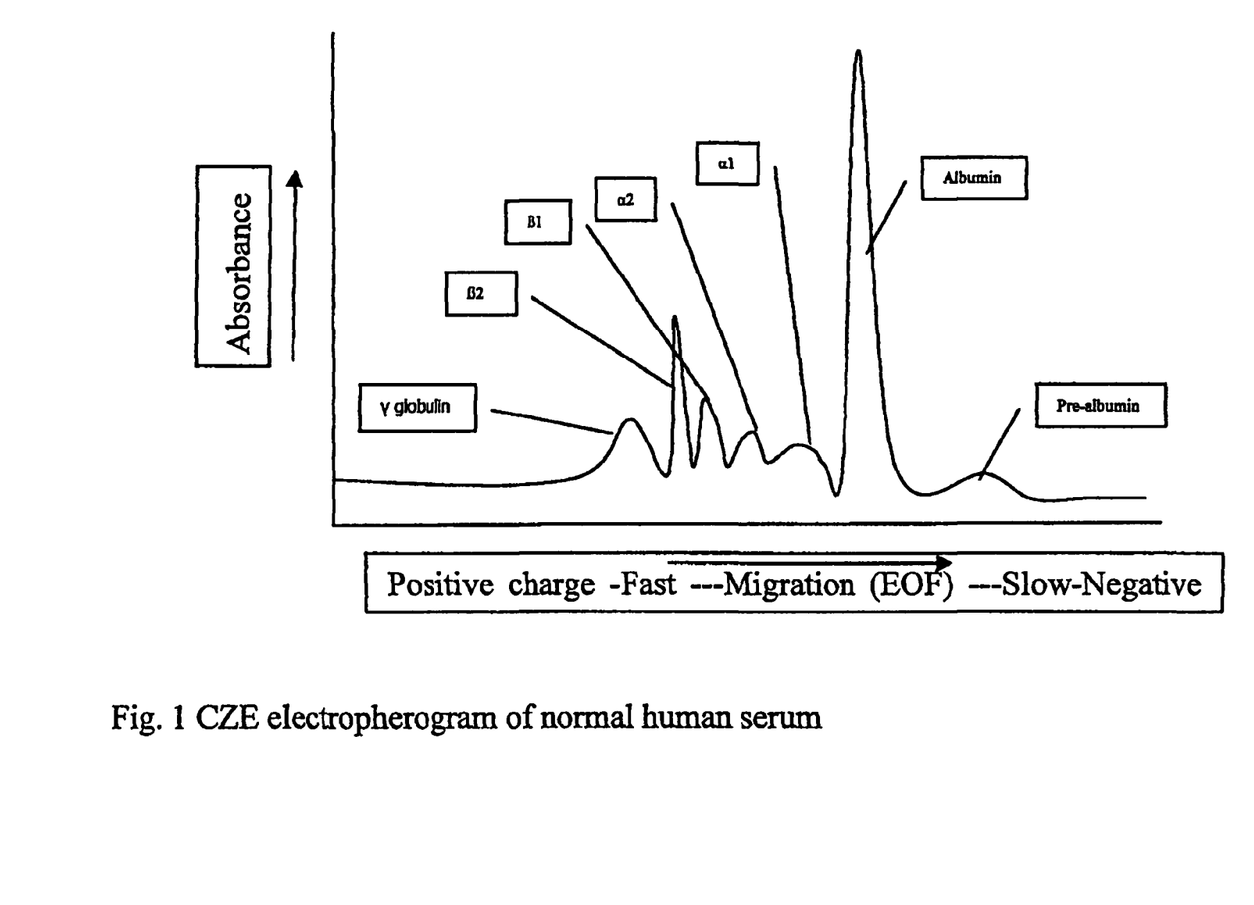
FIG. 1 shows a CZE electropherogram of normal human serum.

FIG. 1 shows a typical CZE electropherogram of serum using conventional CZE.

Since the EOF of the buffer solution is generally greater than that of the electrophoretic flow of the analytes, all analytes are carried along with the buffer solution toward the cathode. Negatively charged analytes are retained longer in the capillary due to their conflicting electrophoretic mobilities.

The narrow bore permits the use of high voltages that increase both the speed and resolution of separation. Direct protein detection is achieved by U.V. measurement at 200 nm, eliminating the need for staining as in the agarose gel methods. The use of automated instruments as offered by Sebia (U.S. Pat. No. 6,780,300) and Helena Laboratories offer the dual advantages of high throughput (multiple samples can be run in parallel) with full automation.

Quantifying and immunotyping of paraproteins has an important role in the diagnosis, classification, and management of plasma cell disorders and other monoclonal gammopathies. CZE can be combined with immunosubtraction or immunodepletion to type the immunoglobulins. (U.S. Pat. No. 5,228,960). The sample is treated with specific antibodies to precipitate and remove the corresponding immunoglobulin, depending on the method; either by spinning out the precipitate off-line or forming a complex that migrates away from its normal migration position. The specific immunotype is revealed as a reduction of the peak on CZE. Studies have shown that these methods are a good alternative for agarose gel electrophoresis and IFE and have reliable performance for paraprotein identification and quantification. (Gay-Bellile et al. 2003 Clin. Chem. 49(11), 1909-1915; Yang et al. 2007 Am. J. Clin. Pathol. 128(2), 293-299; McCudden et al. 2008 Am. J. Clin. Pathol 129(3), 451-458). However, the latter two documents conclude that monoclonal proteins require IFE to be used to characterise them.

Monoclonal immunoglobulins form recognisable peaks with a sensitivity limit of 200-400 mg/L. Monoclonal FLC form recognisable peaks with a sensitivity limit of ca 500-2000 mg/L Monoclonal immunoglobulin proteins which form a recognisable peak may then be "typed" by immunosubtraction.

The level of sensitivity and specificity of the current CZE plus immunosubtraction or immunodepletion methods falls short of that required for the accurate identification and quantitation for serum free light chains. Antibodies typically used for immunosubtraction are currently directed to total light chain rather than being specific for free light chain (FLC). Determination by immunosubtraction/depletion reading protein concentrations at a wavelength of 214 or 200 nm limits these assays to sensitivity to approximately 500 mg/L.

SPE or serum CZE are effective techniques for the identification of monoclonal intact immunoglobulins, such as IgGλ or IgGκ. The drawback with such techniques, as a screen for plasma cell disorders, is that they will miss some cases of light chain only myeloma and AL amyloidosis. It is estimated by the Applicant that about a third to a half of all light chain only myelomas will be missed by conventional CZE which will not detect FLC if insufficient FLC is present in the sample. Therefore, the current best practice is to use separate nephelometric assays for FLC in serum samples, or the identification of monoclonal FLC in urine samples alongside SPE/serum CZE.

The Applicant has identified that a single assay system, capable of detecting monoclonal intact immunoglobulins and monoclonal FLC would be advantageous.

Combining the principles of CZE with those of specific immunoassays combined with sensitive detection methods such as laser induced fluorescence (LIF) and a combined optical system would further enhance the potential of an automated instrument for the simultaneous detection of multiple analytes particularly the simultaneous detection of monoclonal immunoglobulins and the quantification of FLC.

According to the first aspect of the invention, it provides a method of detecting free light chains (FLCs) comprising:
(i) providing a sample from a subject;
(ii) mixing the sample with an anti-FLC specific antibody, or fragments thereof capable of specifically binding the FLC, to form a mixture;
(iii) passing the mixture through a capillary tube by capillary zone electrophoresis (CZE); and
(iv) detecting the presence of the antibody or fragment thereof after passage through at least a portion of the capillary tube.

CZE may be used to detect intact monoclonal immunoglobulin. For example the sample passing through the capillary tube may have the absorbance at, for example, 214 nm or 200 nm measured to detect the passing of the intact immunoglobulin in the sample.

Preferably the antibody or fragment is anti-FLC, especially anti-lambda or anti-kappa FLC specific The ratio of κFLC:λFLC may be determined. This is of use, for example to detect or monitor malignant plasma cell diseases such as multiple myeloma.

The sample is typically a sample of serum, for example human serum. Serum may be obtained from a patient exhibiting symptoms of multiple myeloma.

The antibodies used may be monoclonal or polyclonal antibodies. The antibodies may be FLC-type specific to either lambda or kappa FLC, or alternatively be capable of detecting both lambda and kappa light chains. Total FLC may be measured or individual amounts of lambda and kappa FLC. Such antibodies are generally known in the art and available from The Binding Site Ltd, Birmingham UK.

Fragments of the antibodies may be used. Such antibodies are still capable of specifically binding FLC types immunoglobulins. The antibody fragments may be, for example, Fab, (Fab)$_2$ or other fragments of antibodies.

The antibody or fragment thereof may be labelled. The label may be a label generally known in the art, such as a radio label or a colorimetric label, such as a fluorescent label. Preferably the label is a fluorescent label, including those generally known in the art which are capable of laser induced fluorescence.

Preferably laser induced fluorescence is used to detect the presence of the label.

Other components of the sample, such as γ globulin or albumin, may be detected by measuring the absorbance of the sample after passing through at least a portion of the column, for example by measuring the absorbance at 200 nm.

The method used may be a direct assay in which the antibody or antibody fragment is labelled and mixed with the sample and an immune complex is formed when the antibody binds to the target protein (if present). In this system, typically two peaks will be produced, one with the labelled antibody attached to the target and the other unbound labelled antibody. In such a system the complex peak area or height will be proportional to the concentration of the FLC in the sample.

Alternatively, a competition assay may be utilised. Preferably the sample is additionally mixed with a predetermined amount of the FLC to which the antibody or fragment thereof is capable of specifically binding. Fragments of such immunoglobulins may also be utilised if they are still capable of being specifically bound by the antibody or fragment thereof. This competing target protein is mixed with a test sample. The antibody used may be unlabelled or labelled. Where the competition assay uses an unlabelled antibody and labelled predetermined target protein, two peaks may be observed, one of a complex of labelled competing FLC and unlabelled antibody, and one of unbound labelled FLC. If both antibody and the predetermined FLC are labelled, then potentially three peaks may be observed consisting of a complex of labelled competing FLC with labelled antibody, unbound labelled antibody and unbound labelled FLC. In either case the peak area or height of the FLC/antibody complex would be inversely proportional to the concentration of the FLC being tested for in the sample.

Two different antibodies may be utilised to allow different FLC types to be identified at the same time. In such a situation the antibodies and/or predetermined FLC (or fragments thereof) may be labelled with different labels to allow the substantially simultaneous detection of the different proteins from the same sample.

The methods of labelling antibodies are generally known in the art and are readily available commercially and have been previously used for CZE immunoassay.

Amine-reactive probes have been previously used to modify proteins. Most proteins have lysine (K) amino acids which have exposed amino side chains. Additionally many proteins have an accessible free amine at the N-terminus. These can be used with amine-reactive probes, for example in the pH range of 7-9. For example, reaction with succinimidyl ester reactive fluorophores has been used, resulting in a stable amine bond. Preferably the fluorophores employed herein are fluorescein (FITC) (succinimidyl ester available from Molecular Probes) and DyLight 488 (NHS ester, available from Pierce) are utilised. The excitation (494 nm) and emission wavelengths (4518 nm) wavelengths are the same. However different probes with different excitation and emission wavelengths may be utilised to allow simultaneous detection of different immunoglobulins.

Separation of proteins in CZE is dependent upon the charge/mass ratio. It is possible to alter the charges on the proteins moving through the CZE column by utilisation of different buffers, for example with different pH.

The antibodies used or additional predetermined target proteins added may be chemically modified, for example by acetylation with acetic anhydride or succinylation with succinic anhydride. The former converts a positive to a neutral group and the latter converts a positive to a negative group.

Positive charges may be accomplished by the amidation of carboxyl groups on aspartic and glutamic acid residues, for example by reacting with 1-ethyl-3-(3-dimethylaminopropyl)carbodiimide (EDC) in ethyenediamine dihydrochloride.

Such reactions are generally known in the art.

The attachment of polyethylene glycol (PEG) chains onto the antibodies or predetermined target proteins may also be used to alter the hydrodynamic radius of the molecule. The so-called PEGylation of proteins is generally well-known in the art. For example, N-hydroxysuccinimide-activated PEG (NHS-PEG) is commercially available from a number of suppliers.

Modification of the mobility of the antibodies or proteins helps to fine-tune or assist the separation of the peaks observed.

An alternative way of adjusting the charge would be the production and use of labels having at one end a protein reactive group, such as succinimide or maleimide, attached via a charged polyamino acid linker to a fluorophore. The poly amino acid may, for example, be negatively charged, such as poly(aspartic acid) or positively charged such as poly(lysine). The fluorophore may be one of those previously discussed above. Such labels may be made using conventional protein chemistry.

Accordingly, preferably the label is attached to the antibody, antibody fragment, FLC or fragment thereof, via a charged linker. The charged linker may be poly(aspartic acid) or poly(lysine).

Charge-modified anti-FLC specific antibody, or fragments thereof capable of specifically binding the immunoglobulin, and charge modified target proteins for use in competition assays are also provided. They be modified using one of the techniques discussed above. They may be chemically modified, for example by acetylation with acetic anhydride or succinylation with succinic anhydride. Positive charges may be accomplished by the amidation of carboxyl groups on aspartic and glutamic acid residues, for example by reacting with 1-ethyl-3-(3-dimethylaminopropyl)carbodiimide (EDC) in ethyenediamine dihydrochloride.

Other methods of altering the antibody or predetermined (competing) FLC, to modify their mobility during CZE, may also be used. These could include conjugation to microparticles or dyes for example.

The labels exemplified below are Dylight 488 and fluorescein which both use the same wavelength. For a dual system, one may select two wavelengths at opposite ends of the spectrum, i.e. one red and one green examples are listed below:

| Green | | |
|---|---|---|
| Dye | Excitation wavelength (nm) | Emission wavelength(nm) |
| Cy2 | 489 | 503 |
| FITC | 495 | 517 |
| Dylight 488 | 493 | 518 |
| Alexafluor 488 | 488 | 520 |

| Red | | |
|---|---|---|
| Dye | Excitation wavelength(nm) | Emission wavelength(nm) |
| Cy5 | 650 | 670 |
| Texas red | 596 | 620 |
| Dylight 633 | 638 | 658 |
| Alexafluor 633 | 632 | 650 |

One also needs to consider their stability under different pH conditions, as the CZE buffer system is alkaline, stability between pH 8-11 is desirable.

The ability to simultaneously detect two different analytes improves the assay. Two different analytes used with a conventional capillary having a detection aperture may be used. In such a system the excitation and detection wavelengths are rapidly changed between the two or more different excitation and emission wavelengths for the different fluorophores used in the assay.

Alternatively, a dual aperture capillary may be used with two different detection windows. One of the detection windows is used for, for example, the first fluorophore and the second is used, for example, for the second fluorophore. Each of the fluorophores is excited and detected at their own emission wavelengths, for example via laser induced fluorescence.

Accordingly, preferably the capillary tube may comprise two different detection apertures.

The CZE may also be used to simultaneously produce an electropherogram of the sample by measuring the absorbance, for example at 200 nm or 214 nm.

Accordingly, the immunoassay may also comprise the step of detecting the absorbance of the sample after having been passed through at least a portion of the capillary. The use of a dual-window capillary would also allow the possibility of having one window utilised for detecting the fluorescence of the sample, with the second window utilised for detecting the absorption of the sample.

As already discussed, the separation of the various proteins may be improved by adjusting the pH of the buffer in which the sample is mixed, prior to running through the capillary tube by CZE.

Typically, borate buffers of pH 7-11 are utilised. Preferably the concentration of borate used is up to 500 mM.

The effect of the pH and molarity of a buffer, applied current and speed of separation is discussed in the article by Relf et al (Anal. Chem. (1994) 66, 4227-4033).

The addition of materials, such as PEG, to reduce the absorption of protein on the column may be used. Additionally, it is generally known to add taurine for example at 2.5 mM to decrease the required current.

Anionic surfactants, such as SDS, sodium deoxycholate and related compounds have been shown to improve the separation of peaks in CZE (see Huang et al (J. Proteome Res (2006) 5, 429-36).

Typically the buffer is 20-200 mM boric acid, most preferably 50 mM. A pH modifier such as sodium or lithium hydroxide is added to produce the desired pH. Most preferably the pH is 9-11.

The capillary tube may be a silica capillary tube. This may be coated with, for example, poly(diallyldimethylammonium)chloride (PDADMAC). Such coatings have been used to prevent protein binding (Guzman et at (J. Chromatogr (1992) 608, 197-204).

The invention also provides a capillary tube for the use on CZE comprising two or more detection apertures.

A further aspect to the invention provides a CZE kit comprising a capillary tube, at least one anti-FLC antibody, or fragment thereof.

The antibody may be fluorescently labelled. The kit may additionally comprise one or more predetermined target proteins or fragments thereof, as described above, to allow a competition assay to be produced. The kit may additionally comprise a capillary tube as defined above. The kit may be supplied with one or more buffers to be mixed with a sample.

A further aspect of the invention provides a CZE device comprising a capillary tube according to the invention or a kit according to the invention. The CZE device may comprise a dual wavelength excitation emitter and fluorescence detector.

The invention also provides a CZE device adapted to simultaneously detect the fluorescence from a fluorescent label from a CZE assay, whilst at the same time detecting the absorption of protein from within a sample undergoing CZE.

A further aspect of the invention provides a CZE device comprising a capillary and a dual wavelength excitation emitter and a fluorescence detector, optionally in combination with a protein absorption detector.

A still further aspect of the invention provides an anti-FLC antibody or fragment thereof attached to a fluorescent label via a polyamino acid charged linker. The linker may be poly(lysine) or poly(aspartic acid). The fluorescent label may be as defined above.

CZE kits and devices comprising such antibodies are also provided.

The assay may also be used to detect heavy chain class, light chain type (HC class, LC-type) immunoglobulins instead of or in addition to detecting FLCs. The antibodies may be substituted accordingly in the statements above.

The antibody may also be specific for a heavy chain class at the same time as being specific for a light chain type. Such antibodies or fragments thereof may be used, for example, to discriminate between, for example, IgA κ and IgA λ or IgG κ and IgG λ. Such antibodies may additionally be subclass specific. For example, they may be specific for IgA 1 or IgA 2 or alternatively IgG 1, IgG 2, IgG 3 or IgG 4 subclasses. Such antibodies are known in the art and are available under the trade name "Hevylite" from The Binding Site Ltd, Birmingham, UK.

The invention will now be described by way of example only with reference to the following figures.

METHODS

CZE Assay

There follows a summary of the separation conditions used and examples that demonstrate the proof of principle of these assays for the detection of FLC to the target sensitivity.

All development assays have been performed on a Beckman PACE MDQ system with 488 nm LIF unit. The columns were purchased from Analis 30 cm length (10 cm to detector aperture), 25 um bare faced capillary.

The separation voltage unless otherwise noted was 7 KV for 6.5 minutes which resulted in a current of 10 mA, column temperature was maintained at 32° C.

Column preconditioning was performed between each run with each pressure rinse at 20 psi. Firstly 4.3M urea for 2 minutes followed by water 2 minutes, then 0.1M NaOH 2 minutes and finally run buffer for 2 minutes.

The final run buffer was 150 mM Boric acid adjusted to pH9.9 with 1M NaOH. Sample buffer was TBS ELISA PBS wash buffer type III, working strength buffer was diluted 10× for use as the sample buffer.

| PBS buffer diluted 10X for use as sample buffer | | |
|---|---|---|
| Chemical | Formula | Weight g/L |
| Sodium Chloride (Analar) | NaCl | 7.2 |
| Disodium hydrogen orthophosphate | $Na_2HPO_4$ | 0.161 |

-continued

| PBS buffer diluted 10X for use as sample buffer | | |
|---|---|---|
| Chemical | Formula | Weight g/L |
| Sodium di-hydrogen orthophosphate | $NaH_2PO_4 \cdot 2H_2O$ | 0.01 |
| Tween-20 | — | 0.5 mL |
| Kathon | — | 0.01 mL |
| Water (18.2 MΩ) | $H_2O$ | to 1 L |

Sample injection time was 10 seconds at 0.5 psi pressure, this equates to a sample volume of approximately 15 nL.
Test samples were stored onboard at 10 degrees.
Wavelengths monitored were 200 nm UV or 488 nm fluorescent.
Fluorescent labels used were FITC and DyLight 488.
Anti-λFLC antibody fragments were used to exemplify the invention.

Charged Modification of Antibodies or Antibody Fragments

Negative charge modification can be obtained by conversion of positive amino groups (e.g. on Lysine residues) by acetylation with Acetic anhydride or succinylation with Succinic anhydride. The former modifies a positive to a neutral group (a change of one positive charge, +1 to 0) and the latter converts a positive to a negative group (+1 to −1, a change of two positive charges). The coupling reaction was as follows. The protein to be conjugated at a concentration of 1 mg ml-1 (antibody or FLC) was buffer-exchanged into 0.1 M sodium bicarbonate buffer pH 8.5 by dialysis. To this was added a 5- or 30-fold molar excess (theoretical lysine content) of either Acetic or Succinic anhydride. The mixture was then reacted for 10 min at RT (room temperature) and unreacted anhydride was quenched by the addition of Tris (0.1 M). Finally the sample was desalted and buffer exchanged by dialysis into a suitable buffer for further modification or immunoassay. The molar ratios of reagent were determined experimentally to produce high or low negative charge modification.

Positive charge modification can be accomplished by the amidation of carboxyl groups on Aspartic and Glutamine acid residues. Proteins (1 mg ml-1) dissolved in distilled water were reacted with 2-100 mM 1-Ethyl-3-(3-dimethyl-aminopropyl)carbodiimide (EDC) in the presence of 200 mM Ethylenediamine dihydrochloride for 2 h at RT. The reaction was quenched with Acetic acid and buffer exchanged by dialysis into a suitable buffer. The level of positive charge modification was controlled by the EDC concentration.

Native agarose gel electrophoresis and analytical Anion-exchange chromatography was used for the analysis of the charge-modified proteins.

Immunoassay

Typical conditions used for the assays were:
Run buffer—0.15M Borate pH9.9
Sample buffer—1:10 Type III (PBS)
Column—25 µm i.d. 30 cm Analis bare faced silica
Column temperature 32 degrees
Onboard sample storage temperature 10 degrees C.
Sample load 10 sec at 20 psi
Separation voltage 7 kV for 6.5 minutes
Ramp time 0.5 minute
Base line zero 0.5 mins
Monitor LIF 488 nm
Both competition and indirect assays were studied.

Results

Fab and F(ab)$_2$ labelled with FITC or DyLight 488 nm were found to selectively label the gamma-globulin peak of the electropherogram.

Figure 2:
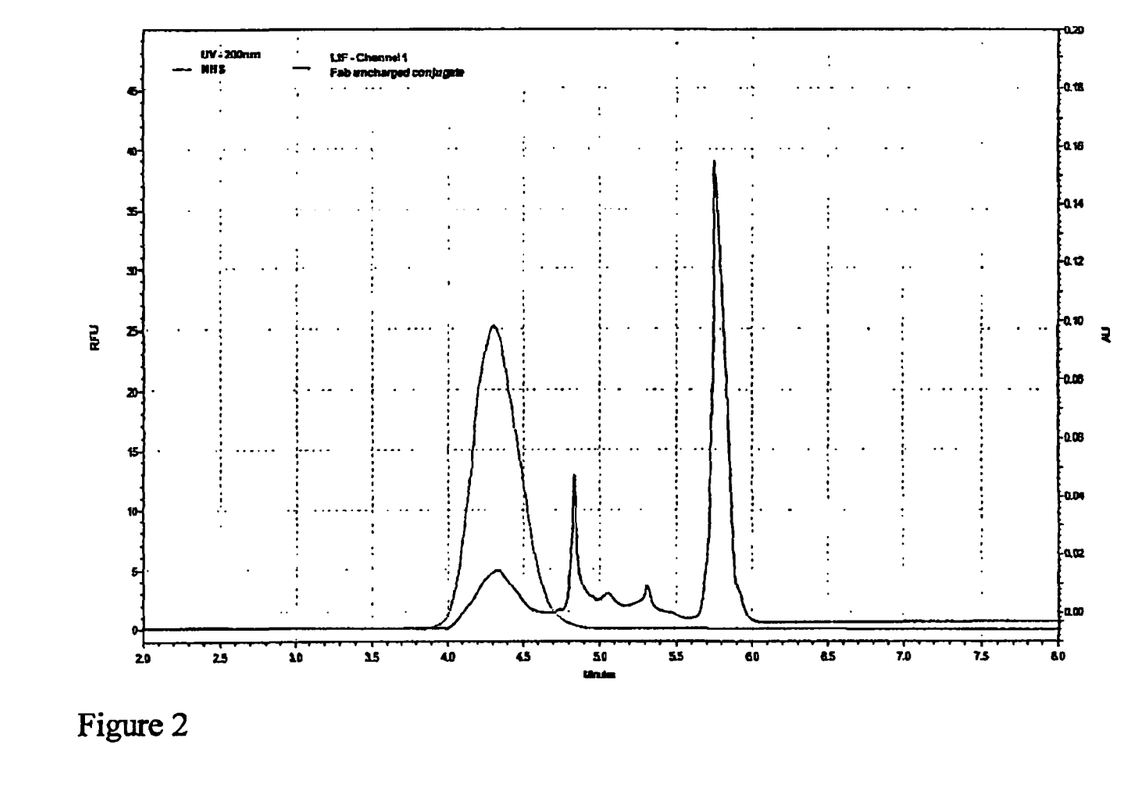
FIG. 2 shows the fluorescence staining of λFLC in the position of the gamma region of the overlaid electropherogram (large peak to left).

FIG. 2 shows an example of an anti λFLC Fab labelled with FITC overlaid in a normal reference serum electropherogram. Separation was run at 25 KV, 50 mM Borate, pH 10.5. Fluorescence was monitored at 488 nm. The area of the peak was found to be a function of the concentration of the λFLC in the sample.

Figure 3:
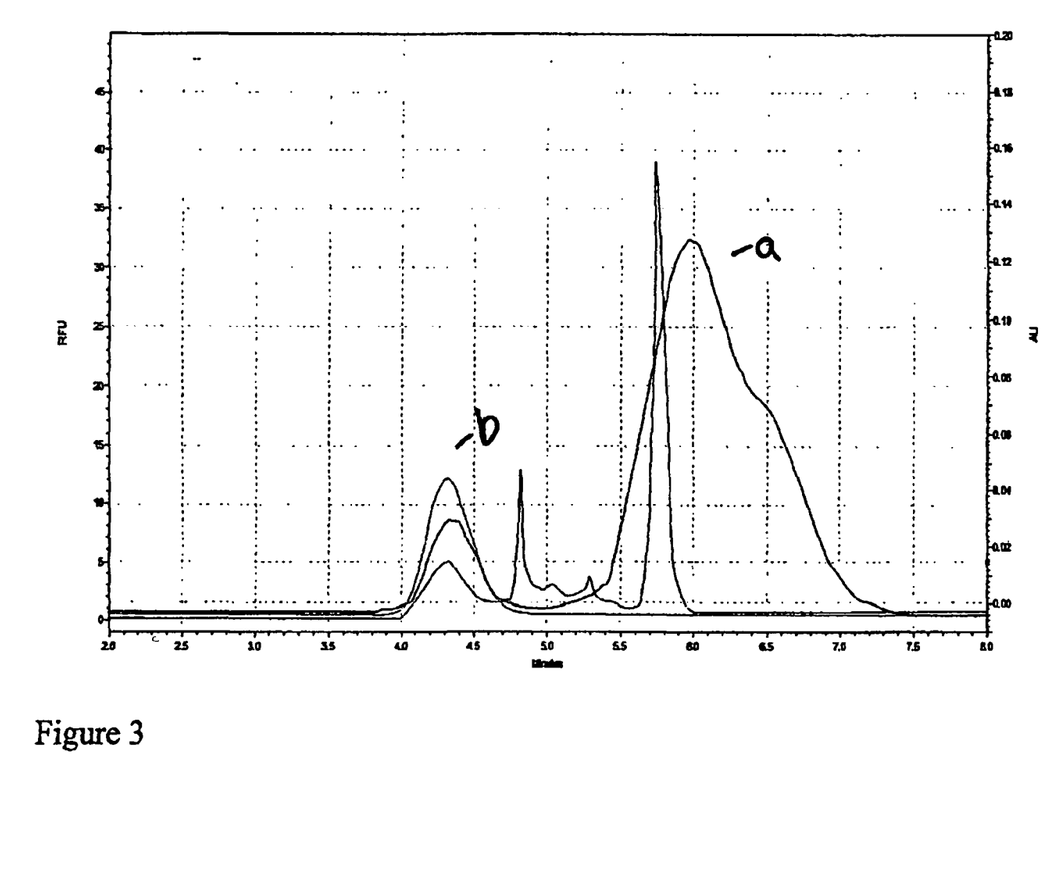
FIG. 3 shows an example of modifying the charge of the labelled antibody, showing the charge in the peak position (a) compared to the uncharged antibody with succinic anhydride (b).

The position of the labelled antibody was found to be adjustable using, for example, succinic anhydride, Fab 100:1 succinic anhydride. This is shown in FIG. 3. Increasingly the charge with succinic anhydride (for example from 30:1 to 1:1), was shown to increase the migration rate of the labelled peak.

Figure 4:
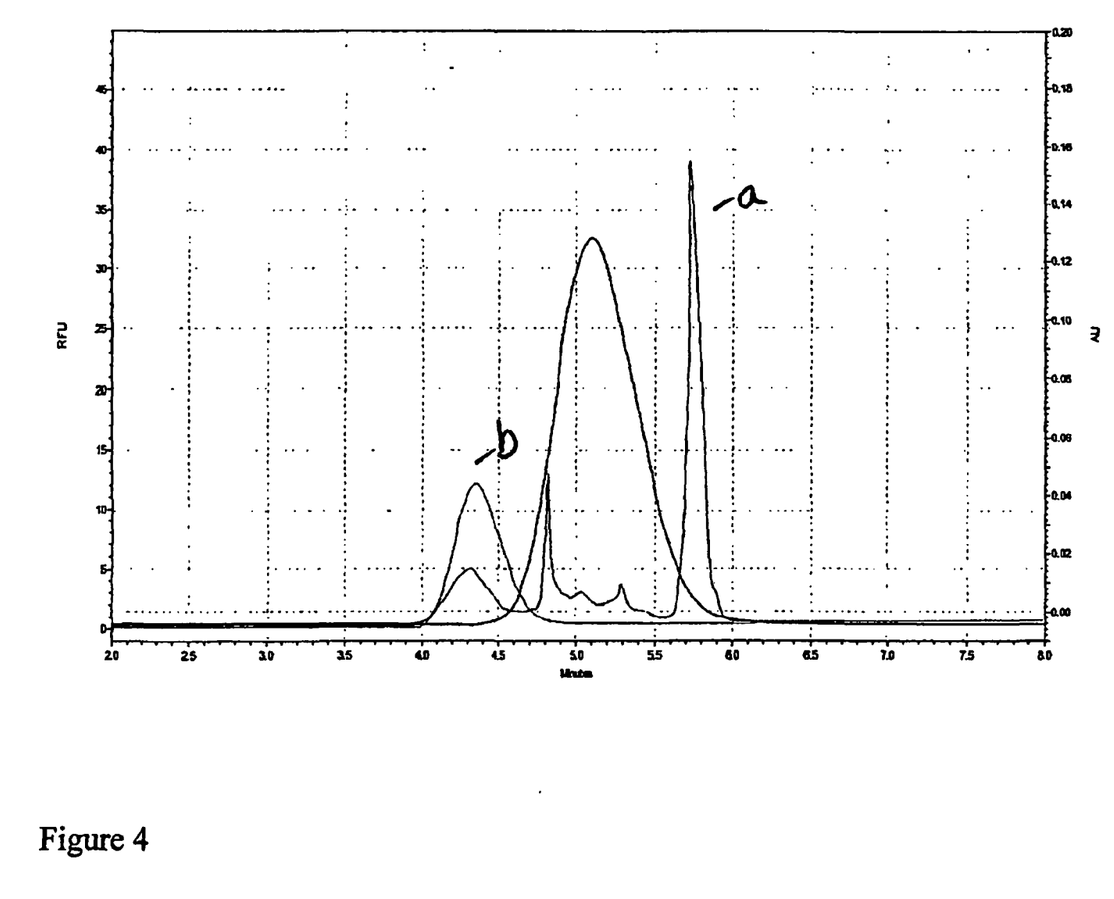
FIG. 4 shows the affect of acetic anhydride on peak position (a) compared to uncharged antibody on an electropherogram (b).

Acetic anhydride (1:1 Fab:acetic anhydride) reduced the speed of the peak through the capillary tube column (FIG. 4).

Figure 5:
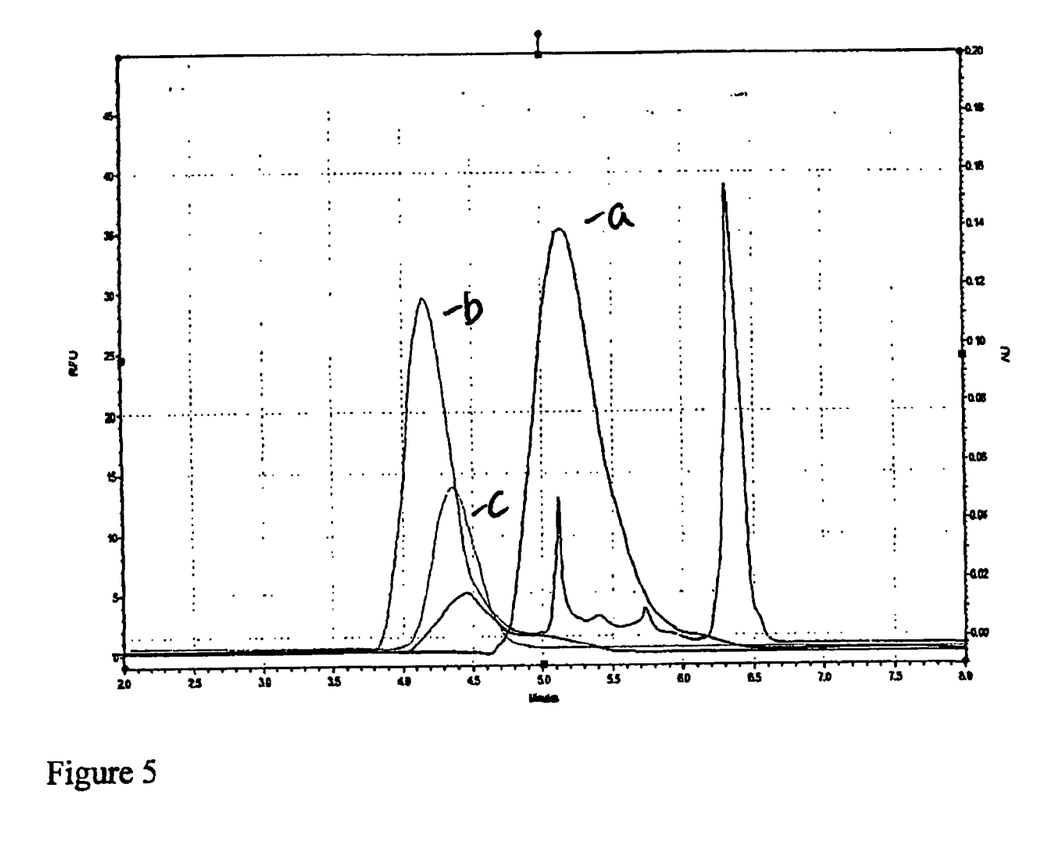
FIG. 5 shows EDC modified F(ab)$_2$ fragments (a) 20 mm, (b) 2 mm compared to an uncharged (c) electropherogram.

EDC was found to increase the rate of movement of F(ab)$_2$ fragments (2 mM EDC), as shown in FIG. 5. This was carried out at 7 KV, 150 mM Borate pH 9.9. Fab fragments were shown to run at the same or slower speed than the gamma region.

Figure 6:
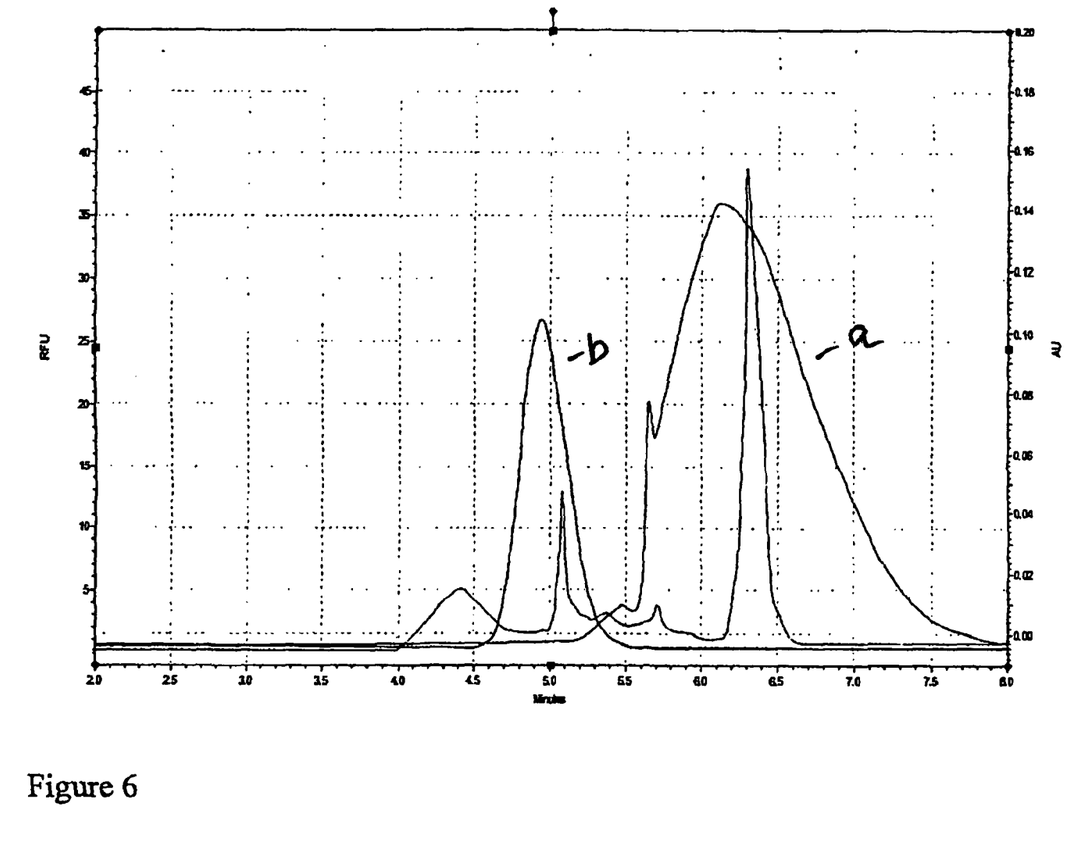
FIG. 6 shows the modification of the charge of IgG with succinic anhydride (a) compared to uncharged (b).

Adding, for example, 5:1 succinic anhydride to IgG, was also shown to increase the rate of migration of the IgG compared to non-modified antibody (FIG. 6).

Immunoassays

F(ab)$_2$ (modified with 4 mM EDC) anti λFLC antibody and labelled λFLC, was compared to different dilutions of antibody. Two peaks were observed. A complex peak and an unlabelled antibody peak.

Figure 7:
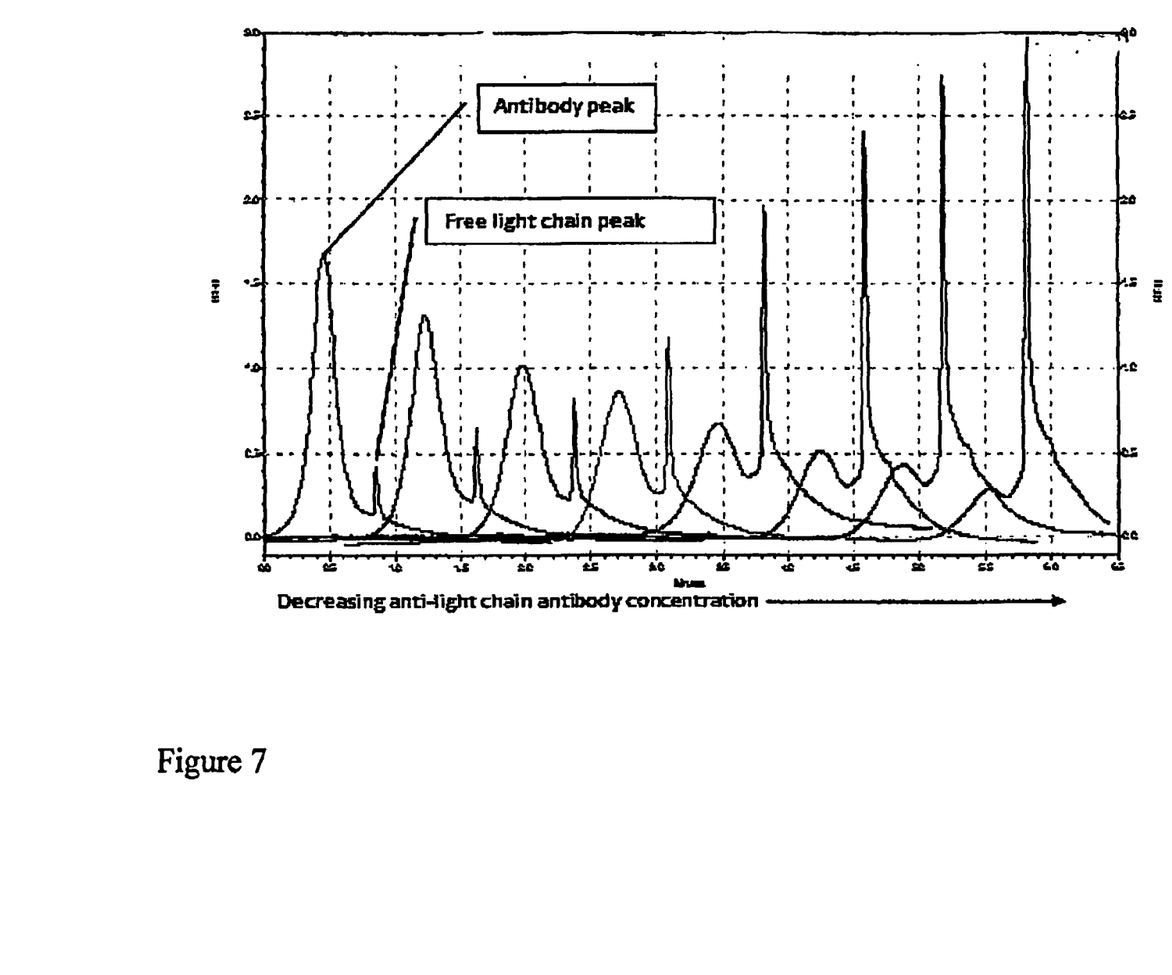
FIG. 7 shows the effect on FLC peak height when mixed with a dilution series of anti-FLC antibody fragments.
Figure 8:
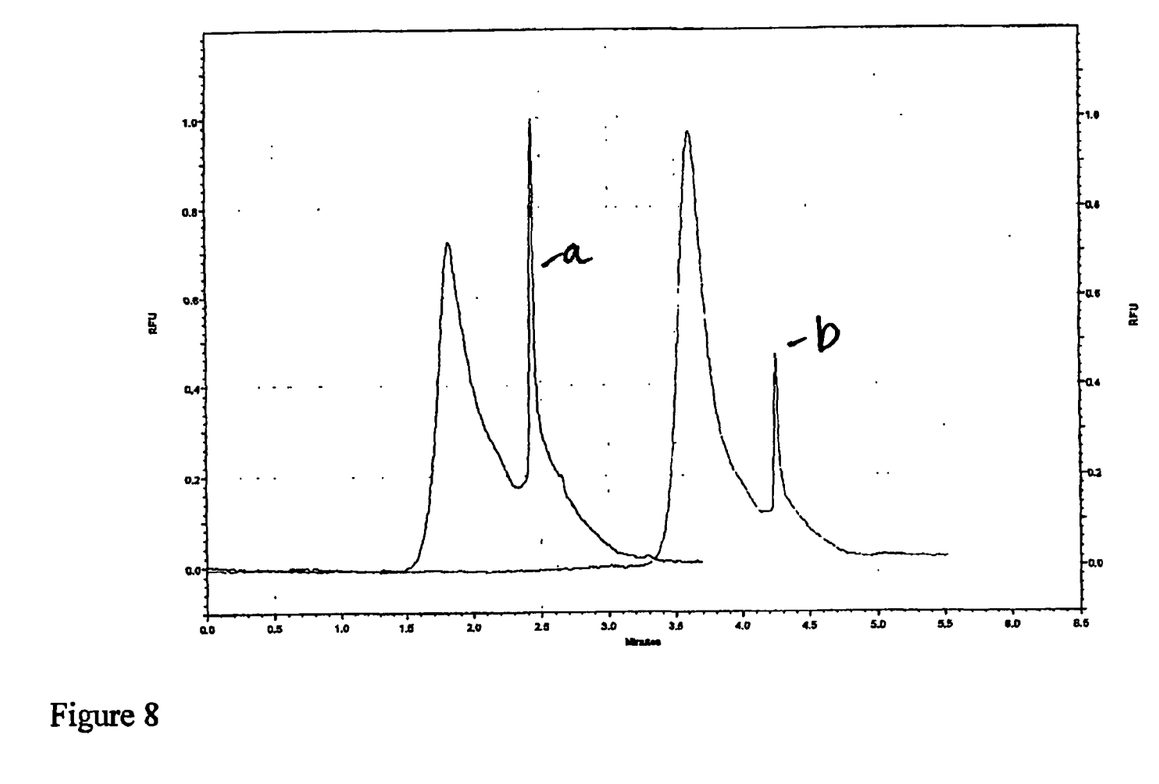
FIG. 8 shows an example of a discreet assay for λFLC using a labelled antibody showing the differentiation in peak height between samples containing 200 (a) and 0 mg/L (b) free light chains.
Figure 9:
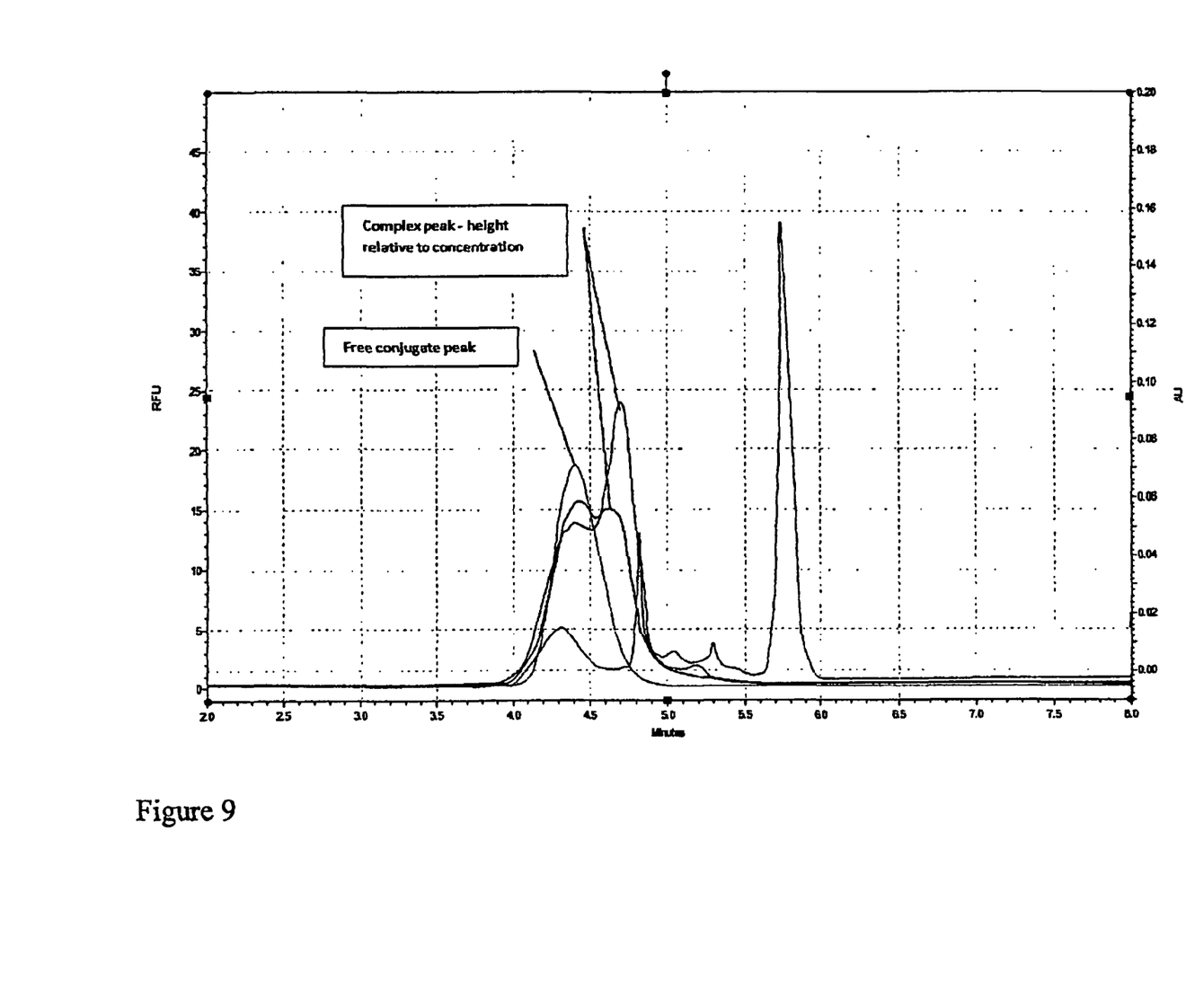
FIG. 9 shows a direct assay for the components of serum using CZE. The absorbance at 200 nm is shown by the line with the large peak (at right of trace). Fluorescence is shown using anti lambda FITC conjugate in comparison with pure lambda light chain at 78 mg/L and 218 mg/L.

The effect of labelled FLC peak height when mixed with a dilution series of anti-FLC, is shown in FIG. 7. This showed that a competition assay, using labelled FLC could be produced A direct assay is shown in FIG. 9.

In the direct assay uncharged whole IgG gave the best result, there was clear differentiation between the free labelled antibody and antibody complexed to the light chain. The use of labelled antibody fragments was less successful as the added charge had an overriding effect on their mobility when complexed with light chain.

CONCLUSIONS

The results show that FLC and other immunoglobulins can be detected using CZE. The immunoassays can be run at the same time as CZE electropherogram to increase the diagnostic information available from such assays.

The invention claimed is:

1. A method of detecting and quantifying free light chains (FLCs) comprising:
   (i) providing a sample from a subject;
   (ii) mixing the sample with
      (a) an anti-FLC specific antibody, or fragments thereof capable of specifically binding the FLC and
      (b) a predetermined amount of a labelled FLC, or a labelled fragment of said FLC, to form a mixture;
   (iii) passing the mixture through a capillary tube by capillary zone electrophoresis (CZE);
   (iv) detecting the presence of the antibody or fragment thereof after passage through at least a portion of the capillary tube;
   (v) measuring the peak area or the height of a FLC/anti-FLC specific antibody complex, and
   (vi) quantifying the peak area or height of the FLC/anti-FLC specific antibody complex, wherein the peak or height of the FLC/anti-FLC specific antibody complex is inversely proportional to the FLC concentration in the sample.

2. A method according to claim 1, wherein intact monoclonal immunoglobulins are additionally detected by CZE.

3. A method according to claim 1, wherein a label is attached to the FLC or the fragment via a charged linker.

4. A method according to claim 3, wherein the charged linker is a poly(aspartic acid) or poly(lysine).

5. A method according to claim 1, wherein the antibody is λFLC or κFLC specific.

6. A method according to claim 1, wherein the anti-FLC specific antibody comprises two antibodies that are mixed with the sample, wherein each of the two antibodies has a specificity for a different FLC type.

7. A method according to claim 6, comprising detecting two different FLC types, using two different antibodies each with a different fluorescent label.

8. A method according to claim 7, wherein the capillary tube comprises two detection apertures.

9. A method according to claim 5 comprising detecting the ratio of κ:λFLC in the sample.

10. The method according to claim 1, wherein the antibody or the antibody fragments is labelled with a fluorescent label.

11. The method according to claim 1, wherein the FLC concentration in the sample is about 200 mg/L or less.

* * * * *